United States Patent [19]
Davidson

[11] 4,120,911
[45] Oct. 17, 1978

[54] METHOD FOR CONCENTRATING A SLURRY CONTAINING A SOLID PARTICULATE COMPONENT

[75] Inventor: James Melvin Davidson, Pinole, Calif.

[73] Assignee: Chevron Research Company, San Francisco, Calif.

[21] Appl. No.: 427,869

[22] Filed: Dec. 26, 1973

Related U.S. Application Data

[63] Continuation-in-part of Ser. No. 204,010, Dec. 2, 1971, abandoned, which is a continuation-in-part of Ser. No. 163,527, Jul. 2, 1971, abandoned.

[51] Int. Cl.² .............................................. C07C 7/14
[52] U.S. Cl. ................................. 260/674 A; 23/296; 62/543; 210/77; 260/674 R; 260/674 N
[58] Field of Search .......... 260/674 R, 674 A, 674 N; 210/77; 23/296, 273, 273 C; 62/58, 543

[56] References Cited

U.S. PATENT DOCUMENTS

| 2,800,411 | 7/1957 | Church | 23/273 |
| 2,820,070 | 1/1958 | Bennett et al. | 260/674 |
| 2,848,519 | 8/1958 | Corneil et al. | 260/674 |
| 3,177,265 | 4/1965 | Lammers | 260/674 |
| 3,467,724 | 9/1969 | Laurich | 260/674 |
| 3,477,575 | 11/1969 | Nemec et al. | 210/77 |

*Primary Examiner*—Delbert E. Gantz
*Assistant Examiner*—C. E. Spresser
*Attorney, Agent, or Firm*—D. A. Newell; John Stoner, Jr.; A. T. Bertolli

[57] ABSTRACT

An improved method for the concentration of a slurry containing a solid particulate component is described. In the method, the slurry is contacted with a rotatable filtration assembly and some liquid is withdrawn from the slurry. When the rotational velocity of the unit is sufficient to develop a substantial centrifugal force at the periphery of the assembly, the process is continuous. The method is especially useful for the concentration of a p-xylene slurry.

20 Claims, 7 Drawing Figures

METHOD FOR CONCENTRATING A SLURRY CONTAINING A SOLID PARTICULATE COMPONENT

CROSS-REFERENCE TO RELATED APPLICATIONS

This application is a continuation-in-part of application Ser. No. 204,010, filed Dec. 2, 1971, now abandoned, which in turn is a continuation-in-part of Ser. No. 163,527, filed July 2, 1971, now abandoned, the disclosures of which are hereby incorporated by reference.

BACKGROUND OF THE INVENTION

1. Field of the Invention

This invention relates to an improved method for the concentration of a liquid-solid slurry containing a solid particulate component. More particularly, it relates to a novel method for the concentration of a slurry comprising a crystalline organic compound and the mother liquor resulting from the crystallization of the compound, especially for the concentration of a p-xylene slurry.

2. Prior Art

The separation of a solid from a slurry of the solid in a carrier liquid is an ordinary operation in the art, for example by filtration, centrifugation, sedimentation, and the like. Usually the equipment employed represents a substantial investment. An objective of the present invention is to reduce the burden on such equipment or the time required by removing a substantial portion of the carrier liquid prior to the final filtration, centrifugation or sedimentation.

The art relating to p-xylene recovery methods has advanced greatly. Larger crystals of p-xylene can now be grown rapidly. The need for an even-purer product has in large part been met. Most process operations have been made more efficient. However, there is yet a substantial room for improvement in certain areas. For example, in the concentration of a p-xylene slurry, blinding and icing of the filter screen is a serious disadvantage. This recurring problem is usually handled by use of a backwash employing a warmed filtrate, by use of mechanical scraping or by a combination of these expedients. By the employment of an in-line filter and a turbulently flowing slurry, longer intervals between the screen-clearing operations have been achieved. But filter-screen plugging and clearance, between the filter screen and stationary parts such as blades or brushes, disrupts the continuity of the processing and is frequently a serious bottleneck for what otherwise could be a continuous process. See, for example, U.S. Pat. Nos. 2,800,411 (use of brushes or backwashing to dislodge filter cake); 2,820,070 (stationary filter); 2,848,519 (stationary filter); 3,177,265 (use of backwashing to dislodge filter cake and conventional centrifuge separators) and 3,477,575 (continuous filtration process in which crystal cake is removed from a rotating filter element by the intensive agitation action generated between the rotating filter element and stationary filter elements or blades).

SUMMARY OF THE INVENTION

A novel method for concentrating a slurry which contains a solid particulate component has been found. This in turn has led to an improved method for recovering a crystalline solid, for example p-xylene, from a liquor which is rich in a crystallizable component.

I have found that a slurry containing a solid particulate component can be concentrated by contacting the slurry with a rotating filtration unit having a filter assembly adapted to pass filtrate while screening out solid, provided that the rotational velocity is sufficient to generate a centrifugal force at the periphery in the range from about 10 to 100 gravitational force units, i.e., G's, and further provided that the density of the solid is greater than the density of the carrier liquid. In the method, the filtrate is collected in a chamber by maintaining a pressure differential between the slurry and the filtrate in the chamber. Surprisingly, when the centrifugal force is adequate, a steady-state cake (as a corollary aspect, a steady-state pressure drop) of solid is established on the filter element of the filtration unit. In the absence of a sufficient force, a compacted solid cake builds up and plugs the unit.

In the method of the present invention, substantially only centrifugal force is used to displace solids from the rotating filtration unit, i.e., from the filter assembly or screen of the rotating filter unit. No blades or brushes or stationary elements or the like are used to displace solids from the filter asssembly. Nor are any stationary elements or blades used to create agitation to cause displacement of the solids from the filter assembly. Actually, however, I have found that rotating baffles are usually desirable to reduce slippage of the liquid in a slippage direction opposite to the direction of rotation. Preferably the rotating baffles rotate at the same speed as the filter assembly. Preferably the baffles are about 2 to 6 in number and extend outward from the center of the filter assembly and split the volume above the filter assembly into about 2 to 6 pie-shaped sectors or compartments.

Although in the process of the present invention the terminology "substantially only centrifugal force is used to displace the solids from the filter assembly" is used, minor factors such as a slippage or washing action of the liquid on the filter assembly can enter into displacement of the solids from the filter assembly. Thus, in addition to centrifugal force activity to remove the solids, there is also some washing action resulting from the filter assembly rotating through the liquid slurry. Although some rotary motion is imparted to the liquid, the filters have a greater or faster motion, and thus there is a relative motion of filter through the liquid.

By a "gravitational force unit," as used herein, is meant by definition the standard acceleration force due to gravity.

By a "slurry containing a solid particulate component," as used herein, is meant by definition a mixture of solid (discontinuous phase) and a liquid (continuous phase).

By a "liquor rich in a crystallizable component," as used herein, is meant by definition a liquid from which a crystalline solid separates when the liquor is cooled and/or evaporated.

THE DRAWINGS

Referring now to the drawings.

Figure 3:
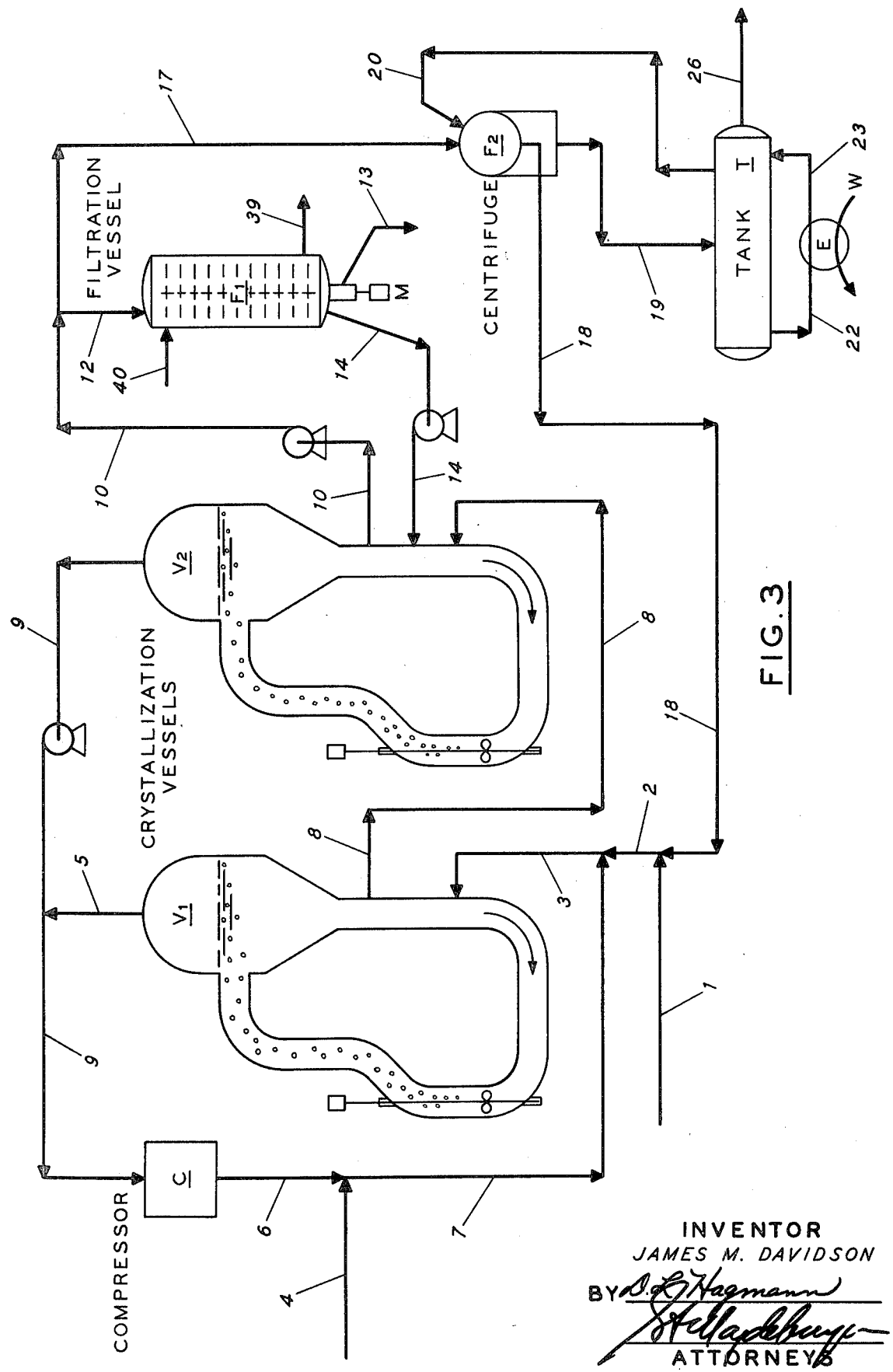

FIG. 3 is a schematic representation of one embodiment of the invention as applied to the process of U.S. Pat. No. 3,457,724.

Figure 4:
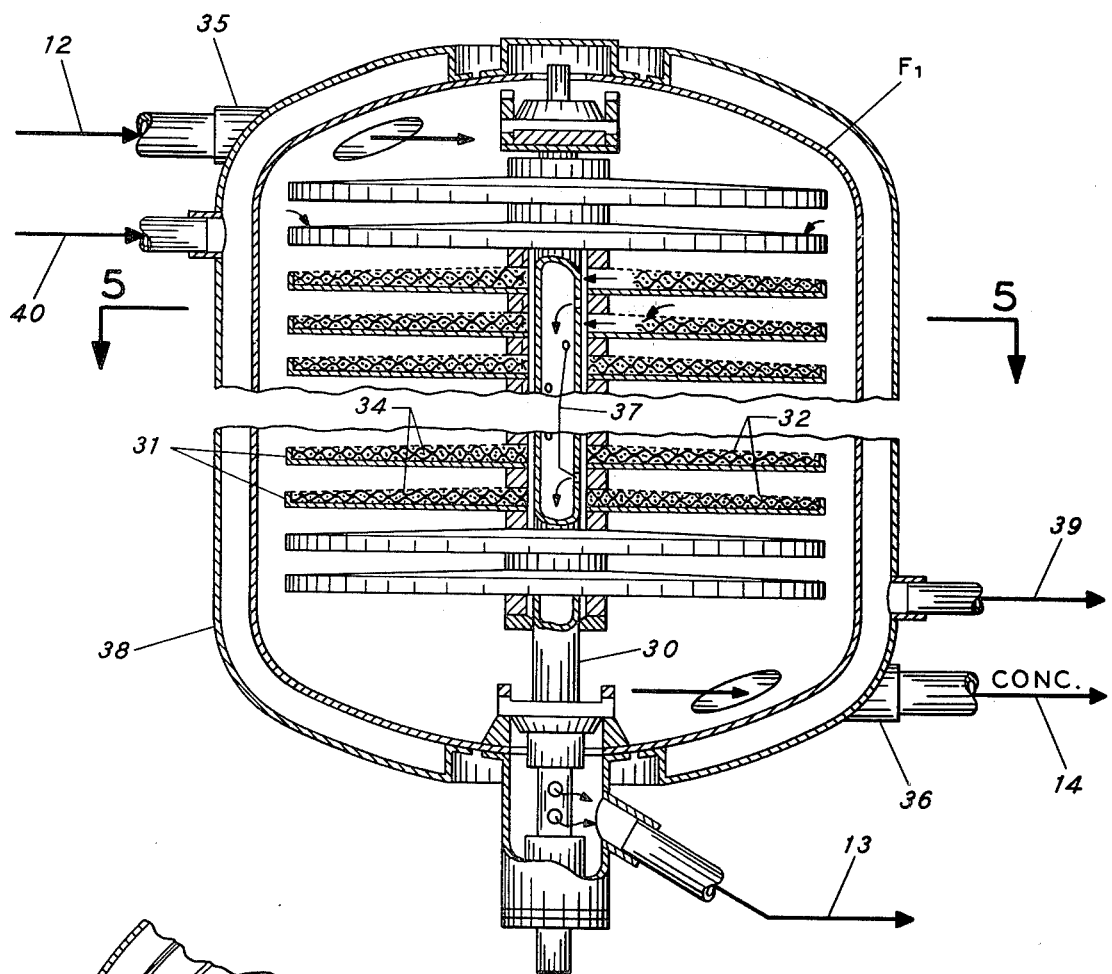

FIG. 4 is a representation, a vertical section, of an embodiment of a rotatable filter unit useful in the practice of the invention.

Figure 5:
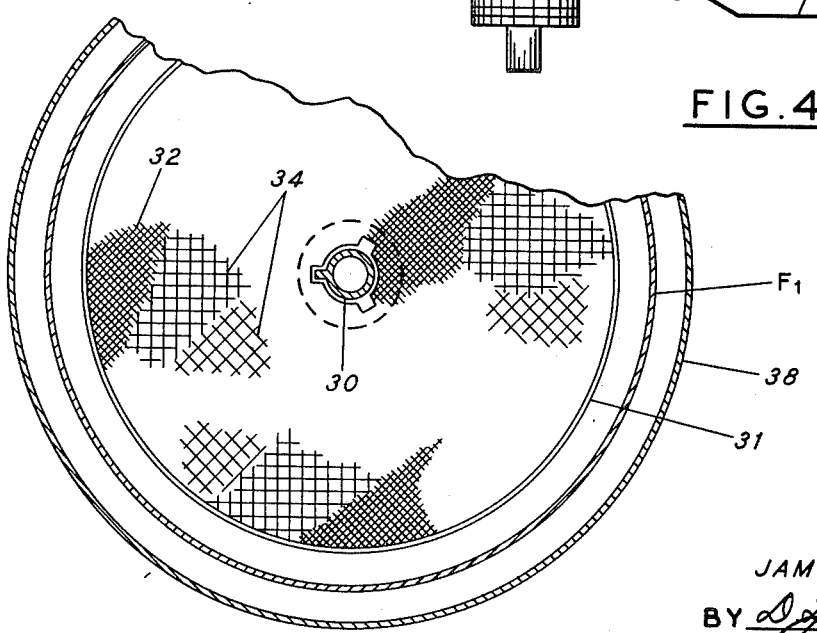

FIG. 5 represents a horizontal section of the unit of FIG. 4.

Figure 6:
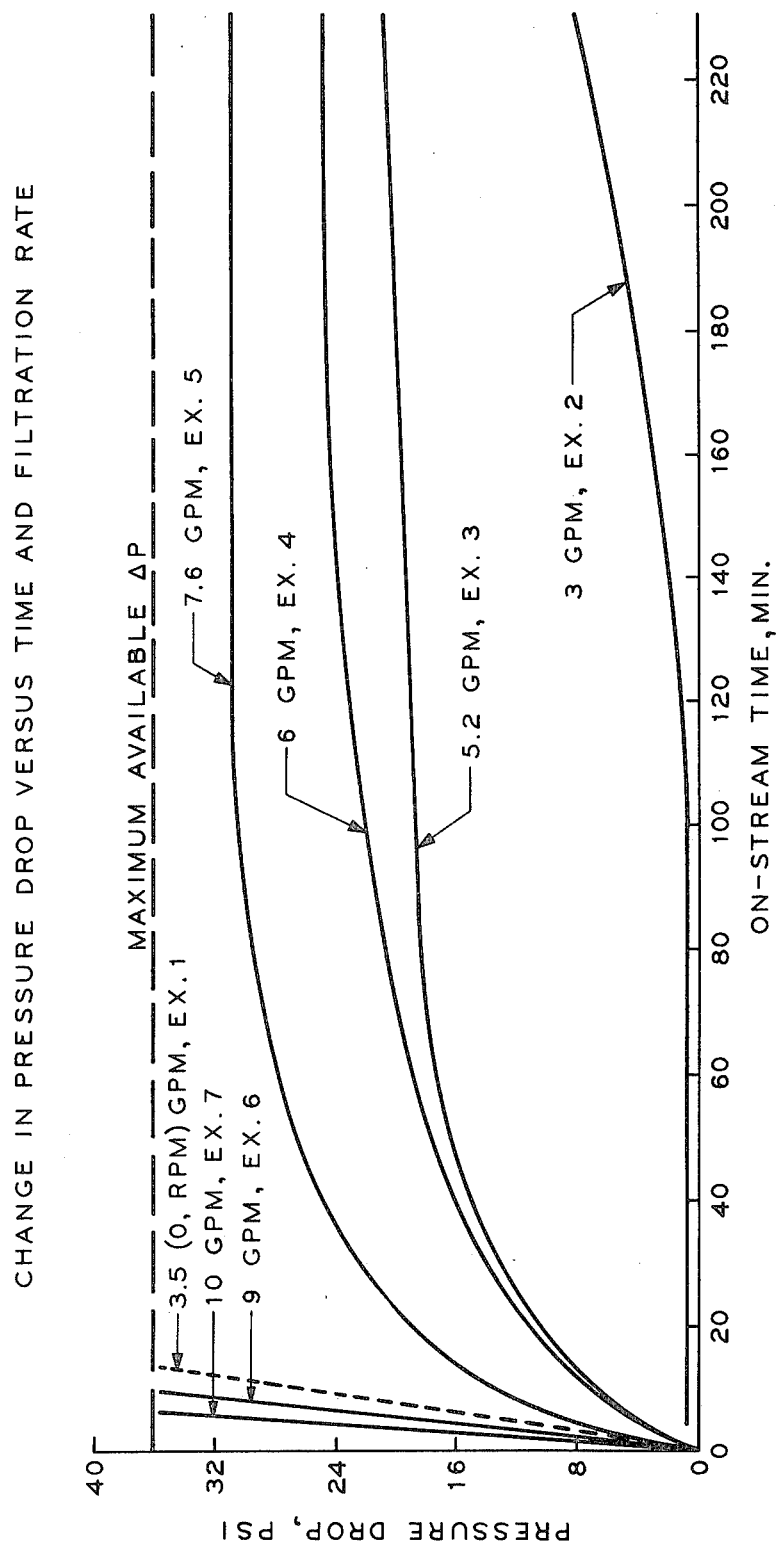
Figure 7:
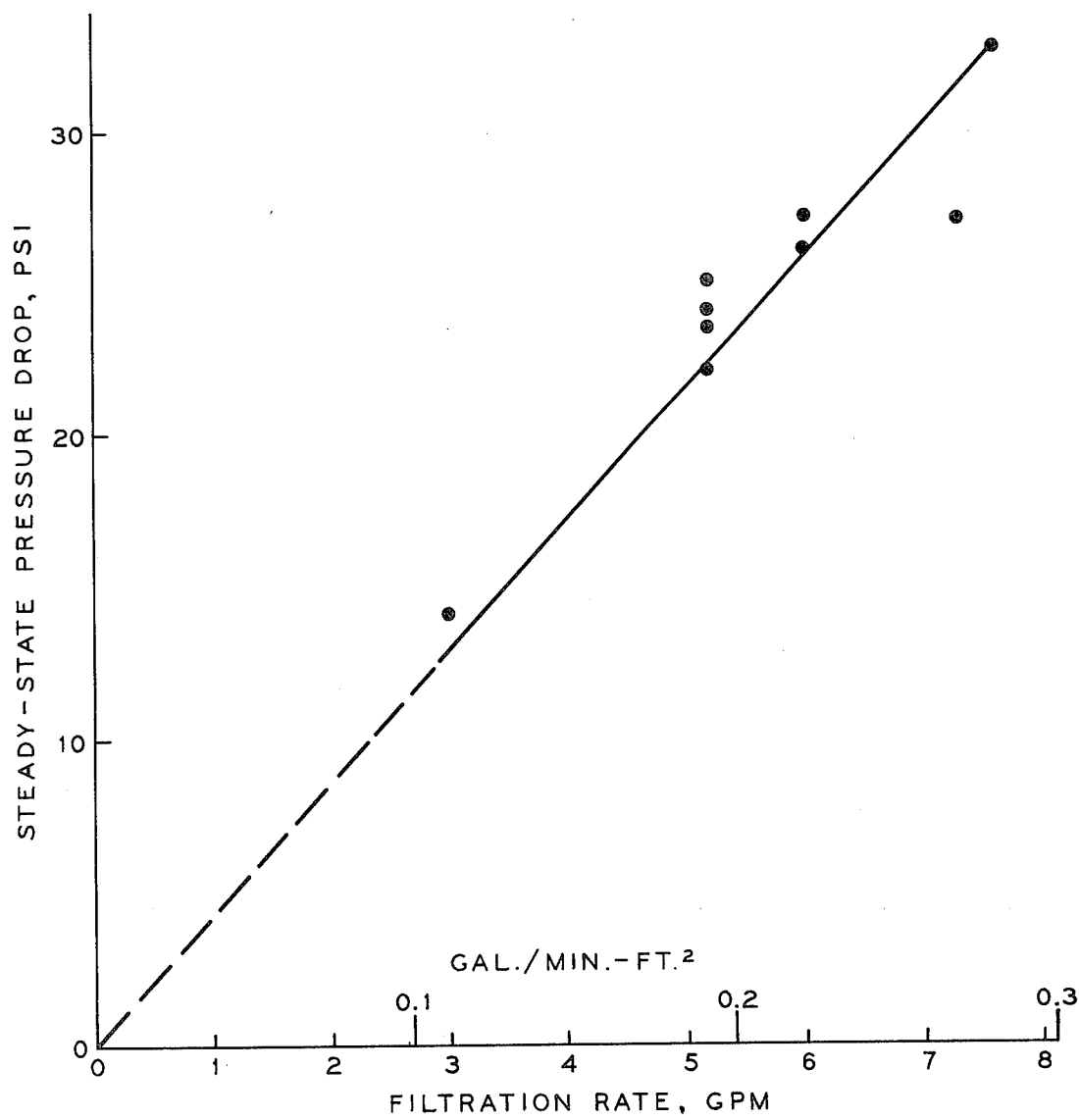

Representative process data are presented in the curves of FIGS. 6 and 7.

EMBODIMENT

Figure 1:
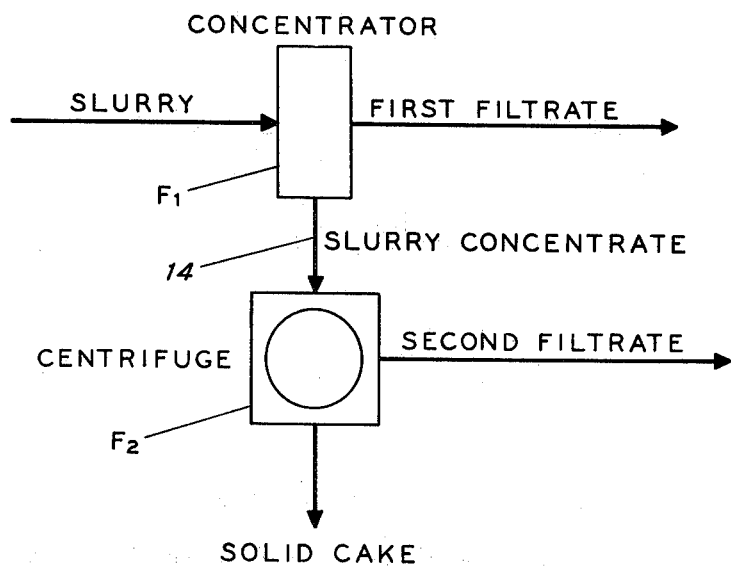
FIG. 1 is a schematic representation of a generalized embodiment of the invention in which a solids-containing slurry is concentrated and the resulting concentrated slurry is delivered to a centrifuge for separation.
Figure 2:
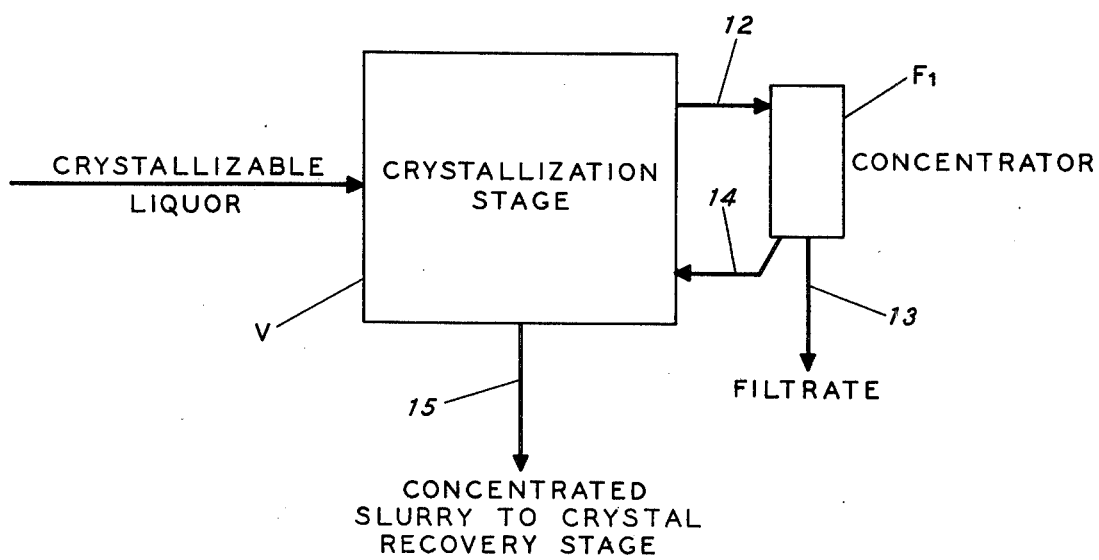
FIG. 2 is also a schematic representation, and in this case a crystals-containing slurry is concentration and the resulting concentrated slurry is recycled to the crystallization zone.

In a preferred embodiment, a slurry containing a crystalline component, for example a slurry in which the crystals have a flat, plate-like configuration, such as a p-xylene slurry, is concentrated as illustrated in the schematic flow process diagram, FIG. 2. Simultaneously, and in amounts sufficient to maintain a constant inventory in the crystallization stage, filtrate and concentrated slurry are removed from the process system via lines 13 and 15, respectively. Slurry is withdrawn from the crystallization stage, V, and passed to the concentrator, $F_1$, via line 12. In the manner described below, a portion of the carrier liquid is separated from the slurry by the action of the concentrator, $F_1$, and the withdrawn liquid is passed via line 13 for suitable disposition, for example to a xylene isomerization unit. The resulting concentrated slurry is withdrawn from concentrator $F_1$ via line 14 and is recycled to the crystallization stage. Via line 15, a super-slurry, i.e., a slurry having a crystalline solids content greater than the slurry obtainable by the simple cooling of a p-xylene-rich liquor, is withdrawn from the crystallization stage, V, and is passed to a suitable recovery stage for solids, for example a centrifuge. Alternatively, in FIG. 1, the concentrated slurry withdrawn from the concentrator, $F_1$, via line 14, is delivered to a centrifuge, $F_2$, for separation and recovery of the solid and filtrate.

In a further alternate mode, p-xylene is recovered by crystallization from a p-xylene-rich liquor in a continuous process employing a two-stage circulating slurry crystallizer section (see, for example, U.S. Pat. No. 3,457,724 — Laurich), as illustrated in the schematic process flow diagram, FIG. 3. The first-stage crystallizer is run at a system pressure of about 2.5 atmospheres, and the second at about 0.4 atmosphere. The higher system pressure facilitates temperature control — the latter improves recovery of refrigerant for recycle. Work expended for this recovery is offset in large part by the further evaporative cooling by the refrigerant at the reduced pressure.

Startup for the process is not difficult, and may be effected by any of a variety of ways known in the art; for example, each unit may be charged with a typical $C_8$ aromatic hydrocarbon stream from a petrolum refinery (15–28% p-xylene, with the balance being mainly m-xylene plus some o-xylene and ethylbenzene, and a small amount of aliphatic hydrocarbon impurities). Liquid carbon dioxide is then injected into each crystallizer while circulating the charge until the desired operating temperatures are reached, i.e., in the process of FIG. 1, about $-75°$ F. in $V_1$ and $-100°$ F. in $V_2$. At these temperatures, each vessel contains a p-xylene slurry.

The next step in the startup is to concentrate the slurry in vessel $V_2$ to a solid p-xylene content of about 30% (weight). Briefly, slurry from crystallizer $V_2$ is concentrated in filtration unit $F_1$, as described hereinbelow, and the concentrated slurry is returned to crystallizer $V_2$ via line 14 while simultaneously passing dilute slurry from $V_1$ to $V_2$, and charging fresh feed and refrigerant into vessel $V_1$ in order to maintain the operational volumes of slurry in both vessels.

In the established continuous operational mode using a feed containing about 20% p-xylene, the following approximate process conditions prevail:

|  | $V_1$ | $V_2$ |
|---|---|---|
| Temperature, ° F. | −70 to −80 | −100 |
| Dissolved $CO_2$, % | 13–15 | 3 |
| Solid p-xylene, % | 6–10 | 30 |
| Pressure, psia, $CO_2$ | 35 | 6 |
| Feed rates (weight) | | |
| Fresh $C_8$, parts/100 parts of slurry | 1 | |
| Refrigerant, parts per part of fresh feed | 0.3 | |

Referring to the process diagram, FIG. 3, fresh feed via line 1 is mixed with a mother-liquor recycle stream from line 18, and to this mixture liquid-carbon-dioxide refrigerant (make-up and recycle, lines 4 and 6) is added via line 7. The combined mixture is then introduced via line 3 into the body of the circulating slurry in the first-stage crystallizer, $V_1$, while the circulation rate for the body of slurry in $V_1$ is maintained at about 1.5–2 turnovers (cycles) per minute. Via line 8, slurry is withdrawn from $V_1$ in an amount sufficient to maintain the input and output material balance in $V_1$.

Carbon dioxide vaporizes in a controlled manner as the slurry rises in the vessel and passes into the void volume at the top of the crystallizers, $V_1$ and $V_2$. The vaporization removes heat energy from the slurries — cools them. By varying the carbon-dioxide pressure in the void volume of the crystallizer, $V_1$, and thus the relative amount of carbon dioxide which can evaporate from the slurry, the temperature of the body of slurry can be conveniently adjusted as desired. Via lines 5 and 9, carbon dioxide gas is removed from the crystallizers and passed to the compressor, C, for recycle to the process.

The main function of the crystallizer, $V_2$, as noted above, is to facilitate the efficient recovery of the refrigerant for recycle. Additional cooling and crystal growth occurs in $V_2$ in connection with this recovery. Circulation of the slurry in vessels $V_1$ and $V_2$ aids in temperature control and also inhibits deposition of solid p-xylene upon the walls of these units. A circulation rate for the slurry in $V_2$ of about 2–3 turnovers (cycles) per minute is desirable.

The filter unit, $F_1$, is a particular aspect of the process of the invention. From the description below and FIG. 4, it is notable that this unit provides for a rapid and efficient withdrawal of mother liquor from the process. Slurry is withdrawn from $V_2$ via line 10 and introduced into $F_1$ via lines 10 and 12. While rotating Filter $F_1$ at a suitable velocity (about 300 rpm for a unit containing 540 ft.$^2$ of screen), mother liquor is removed from the slurry and withdrawn from unit $F_1$ via line 13. The cooling value of the cold effluent mother liquor is recovered by use of indirect heat exchangers (not shown) for the cooling of the fresh process feed.

From vessel $V_2$, a p-xylene slurry having about a 30% solid p-xylene content and containing little or no carbon dioxide is passed via lines 10 and 17 to centrifuge $F_2$ for separation. A solid cake of p-xylene crystals and a mother-liquor fraction are produced. The liquid fraction is withdrawn from $F_2$ via line 18 and recycled to the process. The solid p-xylene is retained in centrifuge $F_2$ and is washed by a portion (about 50 weight percent based upon the solid) of substantially pure p-xylene liquid. The latter is passed to $F_2$ from product storage and melt tank T. The temperature of the product and wash liquid in T is maintain at about 79° F. by means of heat exchanger E and its associated lines, 22 and 23. The washed cake is then transferred to melt tank T via line 19.

The use of the present unique method for the concentration of a crystal-containing slurry, for example a p-xylene slurry, is now described. Refer to FIG. 4. Filter unit $F_1$ is a suitable filtration unit, for example a cylindrical vessel, adapted to support a rotatable hollow shaft 30, and has an inlet port 35 and an outlet port 36 for the tangential (relative to the circumference of the vessel) introduction and withdrawal of p-xylene slurry, an outer shell 38, and associated inlet and outlet lines 39 and 40 for temperature control. About 46 filtration elements 31 are attached to and supported by shaft 30. These elements are fabricated from stainless-steel filter screens (80-micron sized) adapted to form chamber 34, which is connected to the interior of hollow shaft 30 by a suitable means, for example port 37.

In the operational mode, dilute slurry is pumped into $F_1$ via line 12 and port 35, and a relatively concentrated slurry is withdrawn from $F_1$ via port 36 and line 14. By control of the pumping means (not shown), a differential pressure is maintained between the slurry in $F_1$ and chamber 34 in filter elements 31. In a preferred embodiment, a slurry having about a 35% content of solid p-xylene is produced, and unit $F_1$ has the following characteristics:

Total filter screen area, ft.$^2$: 540
Screen diameter, inches: 47
Filter elements: 46
Screen sizing, microns: 80 under the operating conditions:

Pressure differential, atms.: 3
Shaft rotational velocity, rpm: 300
Filtrate removal rate, gpm: 150

PROCESS PARAMETERS

The more important operational requirements for the practice of the invention include:
 (a) a rotatable filter unit;
 (b) an adequate centrifugal force;
 (c) a suitable filter screen;
 (d) an adequate pressure differential; and
 (e) a slurry containing a solid component which has a density greater than that of the carrier liquid.

Other and secondary factors include the temperature, the concentration of the slurry, the configuration of the rotatable filtration unit, and the sizing of the solid.

The filter unit must be a rotatable unit capable of rotation at a high velocity and preferably sufficient for the establishment of a steady-state cake on the filter screen. Stated another way, the unit must be capable of generating a substantial peripheral centrifugal force, preferably sufficient to establish a steady-state (constant) cake, i.e., a force in the range from about 10 to 100 gravitational units. Since the centrifugal force generated depends upon: (1) the speed of the rotation; and (2) the radius of the filter element; the minimal speed required for the steady-state condition varies depending upon the dimensions of the filter unit. Ordinarily, satisfactory rotational velocities for units having practical dimensions are in the range from about 50 to 600 rpm.

The size of the particulate solid may vary widely. The slurry must be susceptible to pumping for satisfactory use of the method. Accordingly, the average diameter of the solid should be in the range below about 6.4 mm. In general, for satisfactory operation herein, the particles will have an average diameter in the range from about 0.037 to 6.4 mm, preferably 0.125 to 1.2 mm.

The sizing of the filter screen may vary over a range, and needs only to be sufficiently fine to permit establishing a steady-state solid cake. Once established, the latter appears to function as an adjunct of the filtering means. In general, the screen size used will depend upon the range of the sizing of the solid and the degree of exclusion of the solid desired for the filtrate. Satisfactory screens have sieve openings in the range from about 0.010 mm to 6.4 mm, preferably 0.010 mm to 1.2 mm, more preferably 0.017 to 0.5 mm.

Practical factors with respect to screen selection relate to the mechanical strength of the screen, the insolubility of the screen in a hydrocarbon or carrier liquid medium, and the like. The screen may be fabricated from metal, cloth, organic plastics, or other suitable material. Metal screens are preferred because of their strength.

The pressure differential (driving force) required to obtain a useful filtration rate varies. In general, there must be a differential pressure between the slurry and the filtrate chamber of at least about 0.5 atmosphere. The rate at which filtrate can be withdrawn from the filtration unit increases as the driving pressure is increased, but this pressure should not be excessive, i.e., it should not exceed the breaking strength of the screen. Usually a driving force in the range from about 0.5 to 10 atmospheres is adequate. The preferred range is 1 to 5 atmospheres.

Solid-liquid slurries, in general, may be concentrated by the method of the invention, provided that the density of the solid is greater than that of the liquid carrier medium. The difference need not be large, yet the larger it is the easier is the concentration. A density differential of about 0.05 g/cc between the solid and liquid is usually adequate.

Slurries having a solid component can, in general, be concentrated by the present method provided that they and the resulting concentrated slurries are pumpable. Whether or not a slurry can be transported by a pump-and-pipe combination varies, depending in particular upon the amount and kind of the solid and upon the type of pump used. In general, a pumpable slurry contains less than about 65 weight percent, preferably less than 55 weight percent, of particulate solid having a particle sizing (average diameter) in the range from about 0.037 to 6.4 mm, i.e., about 3 to 400 mesh (Tyler Standard Screen Scale Sieve). General information relative to pumpable slurries is available by reference to standard chemical engineering texts and handbooks, for example "Perry's Chemical Engineers' Handbook," by R. H. Perry, C. H. Chilton and S. D. Kirkpatrick, McGraw-Hill Book Company.

p-Xylene slurries, in general, can be concentrated by the process provided, of course, that they and the resulting concentrated slurries are pumpable. A slurry which has a solid p-xylene content above about 55 weight percent usually cannot be conveniently transported by means of a pump and transfer line. Thus, the p-xylene slurries contemplated for concentration by the invention herein must have a solid p-xylene content below about 55%. Feeds having a solids content in the range 1 to 40 weight percent are, as a practical matter, most advantageously concentrated by the process.

The liquid carrier component of the p-xylene slurries employed as feeds for the present concentration method may vary widely. The primary requirement in this respect is that the carrier be a liquid or a mixture of liquids. Usually the liquid will be the mother-liquor residue after the formation of p-xylene crystals as the result of the cooling of a p-xylene-rich liquor to a crystal-forming temperature, i.e., in the range from about −110° F. to about 32° F. Other liquids may also be present in the carrier liquid and may be added subsequent to or prior to the concentration or crystallization, as known in the art, for example as adjuvants or washing agents, anti-icing compounds, and the like — such as methanol, acetone, toluene, and the like.

Representative classes of slurries contemplated for concentration by the method of the invention include inorganic and organic crystalline and noncrystalline particulate solids dispersed in carrier fluids. Slurries containing crystalline solids are especially amenable to concentration by the method of the invention. Hence, this class of slurry, and most particularly the class of organic crystalline solid-liquid slurries, is preferred. The fluid (carrier) is often the mother liquor resulting from the cooling and/or evaporation of a liquor which is rich in a crystallizable component.

Representative crystalline inorganic solid components include sodium and potassium chloride, oxalate, ammonium sulfate, and like salts.

Representative crystalline organic solid components include p-xylene, durene, benzene, naphthalene, urea, phthalimide, petroleum wax, benzoic acid, isophthalic acid, terephthalic acid, phthalic anhydride, maleic anhydride, fumaric acid, and like crystalline organic solids. Other representative particulate solid components useful in the process include coal, organic polymers, sewage, manufacturing-plant waste, ore concentrates, and like materials.

A slurry containing an inorganic crystalline component is relatively abrasive compared to a slurry in which the component is organic. Therefore, in terms of wear and tear upon process equipment, the method of the invention is more conveniently applied to the concentration of a slurry containing a crystalline organic component and, again, such are preferred feeds herein.

The carrier liquid component of the slurry may vary widely, depending upon the solid component. The primary requirement is that the carrier be a liquid or a mixture of liquids and have a lower density than the particulate solid component of the slurry. Usually the carrier is any one of a number of suitable solvents or non-solvents and is often the mother-liquor remainder from a conventional crystallization, as known in the art. Water, organic solvents in general, and solvent mixtures are representative carrier liquids.

Secondary process parameters, such as slurry temperature and concentration, as well as the configurational aspects of the unit, are moderating factors relative to the prime variables discussed above. The temperature and concentration parameters relate to viscosity-flow effects. Usually the temperature of the slurry is dictated by conventional and practical considerations, for example by known crystallization requirements. For example, in the formation of a p-xylene slurry, a $C_8$-aromatic hydrocarbon liquor, a petroleum refinery cut, is cooled to a crystallization temperature in the range from about −110° F. to −80° F. In the case of the recovery of a salt from an aqueous salt solution, the slurry temperature will usually be in the range from about 28° F. to 210° F., i.e., above the freezing point and below the boiling point of the particulate solution, and the like.

The configurational aspects, on the other hand, relate to the relative ease of establishing the steady-state solid cakes on the filter screen and to the relative efficiency in space utilization. The position of the filter screen, whether facing up, down or sideways, is not especially material. Similarly, the form of the filtration elements, whether flat, oval, spherical, etc., is not critical. On the other hand, the flat, plate-like form, as depicted in FIG. 4, is preferred. For a given volume, the flat, plate-like structure permits a more efficient use of space. The volume and configuration of the chamber receiving the filtrate may also vary widely. But for the relatively flat, plate-like shape, the chamber is preferably established by a backup plate, one or two layers of large-mesh screen (for example in the range 50- to 100-mm-diameter screen), and finally the filter screen. The plate and filter screen and suitably joined (adapted) to form the boundaries of the chamber. The intermediate screen layers only provide for the separation of the boundary elements.

The following examples further illustrate the invention. The slurry used in the demonstration was a p-xylene slurry. The examples were run in a vertically mounted, rotatable filter unit substantially as described in FIG. 4, except that one side of filter element 31 was 80-micron-sized stainless-steel screen; the other was a solid backup plate; and between the filter and the plate were two intervening layers of larger-mesh screen. The latter established chamber 34. The unit dimensions were as follows:

Internal capacity, gallons: 59.5
Chamber diameter (I.D.), inches: 23.4
Filter-plate diameter, inches: 20
Shaft diameter, inches: 2
Number of filter elements: 13
Total filter-screen area, ft.$^2$: 27
Filter-element spacing, inches: 1.1

The associated auxiliary equipment (not shown) — pumps, temperature and pressure sensors, and the like — were standard items.

The source of the p-xylene slurry used in the runs was the p-xylene crystallization stage of a commercial p-xylene recovery plant. The p-xylene-rich liquor was an aromatic $C_8$ petroleum refinery stream having a p-xylene content of about 21 weight percent and a first eutectic temperature in the range −81° to −90° F.

FILTRATE REMOVAL RATE

EXAMPLES 1-7 p-Xylene slurry at a temperature of about −82° F. was delivered to the concentrator, FIG. 4, at a rate of 15–24 gpm under the conditions and results as noted in Table I below and in FIGS. 6 and 7.

TABLE I

|  | Example Number | | | | | | |
|---|---|---|---|---|---|---|---|
|  | 1 | 2 | 3 | 4 | 5 | 6 | 7 |
| Spin rate, rpm | 0 | 408 | 408 | 408 | 408 | 408 | 408 |
| Filtrate withdrawal rate, gpm | 3.5 | 3 | 5.2 | 6.0 | 7.6 | 9 | 10 |
| Concentrated slurry, wt. % solid p-xylene | — | 32 | 42 | 40 | 43 | 38 | 49* |

*Calculated from feed and slurry analysis

In Examples 1, 6 and 7, after a short run — 7–14 minutes — the pressure drop due to the p-xylene cake buildup on the screens prevented further concentration of the slurry. Example 2 illustrates the operation below the steady-state condition. Examples 3, 4 and 5 illustrate the development of steady-state p-xylene cakes on the filter screens. Example 5 was discontinued after a run of 10 hours, of which about the last 8 hours was at the steady-state condition. The concentration during this period was effected smoothly and continously. The concentrated slurry was recycled to the crystallization unit (alternatively it was an excellent feed for recovery of p-xylene by centrifugation, for example as illustrated in FIG. 2).

The stoppage which occurred in Examples 6 and 7 is believed to be due to the limited pressure differential available. The pump had a low capacity. However, assuming that the high filtration rate prevented reaching the required steady-state condition, then this difficulty can be overcome by increasing the spinning rate, by decreasing the filtration rate, or by a combination of these adjustments.

The p-xylene crystal cake which develops upon the spinning filter screens participates in the filtering action. Thus, in the startup of the concentration operation, the filtrate in the above examples was found to contain a significant amount of microcrystals and the p-xylene content of the filtrate exceeded the amount for the solid-mother liquor equilibrium value. After a short time, and when some cake of solid p-xylene had become established on the filter screens, the p-xylene content of the filtrate was essentially the theoretical value.

In a similar manner, other pumpable slurries containing a particulate solid component are concentrated by the method of the invention.

What is claimed is:

1. A process for increasing the concentration of a slurry comprising a particulate solid in a carrier liquid, which comprises removing a portion of said liquid from the slurry by:
   (1) introducing the slurry into a filtration zone containing a rotating unit, said unit containing a filter assembly adapted to pass said liquid as a filtrate while screening out said solid;
   (2) collecting said filtrate in a chamber in said assembly by maintaining a pressure differential between said slurry in said zone and said filtrate in said chamber;
   (3) withdrawing the filtrate from said chamber; and
   (4) withdrawing the resulting concentrated slurry from said zone;
wherein said solid had a sensity greater than that of said carrier liquid, and wherein said unit is rotated at a velocity sufficient to generate a centrifugal force in the range from about 10 to 100 gravitational units and wherein substantially only centrifugal force is used to displace solids from said filter assembly.

2. A process as in claim 1 wherein said introduction and withdrawals in and out of said zone are coordinated for the maintenance of a substantially constant volume of slurry in said zone.

3. A process as in claim 1 wherein rotational velocity is in the range from about 50 to 600 rpm.

4. A process as in claim 1 wherein said slurry is obtained by the cooling of a liquor rich in a crystallizable component.

5. A process as in claim 1 wherein said velocity is sufficient to establish a steady-state cake in said filter assembly.

6. A process as in claim 1 wherein a metal screen having a size in the range from about 0.010 to 6.4 mm is used for said screening.

7. A process as in claim 1 wherein said slurry has a crystalline solids content in the range below about 65 weight percent.

8. A process as in claim 7 wherein said range is about 1 to 40 weight percent.

9. A process as in claim 1 wherein said filter assembly is substantially of the flat, plate-like configuration.

10. A method for increasing the concentration of a slurry comprising solid p-xylene in a carrier liquid, which comprises removing a portion of said liquid from the slurry by:
    (1) introducing the slurry into a filtration zone containing a rotating unit, said unit containing a filter assembly adapted to pass said liquid as a filtrate while screening out said solid p-xylene;
    (2) collecting said filtrate in a chamber in said assembly by maintaining a pressure differential between said slurry in said zone and said filtrate in said chamber;
    (3) withdrawing the filtrate from said chamber; and
    (4) withdrawing the resulting concentrated slurry from said zone;
wherein said unit is rotated at a velocity sufficient to generate a centrifugal force in the range from about 10 to 100 gravitational units and wherein substantially only centrifugal force is used to displace solids from said filter assembly.

11. The process as in claim 10 wherein said introduction and withdrawals in and out of said zone are coordinated for the maintenance of a substantially constant volume of slurry in said zone.

12. The process as in claim 10 wherein rotational velocity is in the range from about 50 to 600 rpm.

13. The process as in claim 10 wherein said resulting concentrated slurry is divided into two portions, in which the first portion is delivered to a crystallization zone and the second portion is separated by centrifugation into a solid and a liquid fraction.

14. The process as in claim 10 wherein said slurry is obtained by the cooling of a p-xylene-rich liquor.

15. The process as in claim 10 wherein said velocity is sufficient to establish a steady-state pressure drop in said filter assembly.

16. The process as in claim 10 wherein a metal screen having a sieve opening diameter in the range from about 0.010 to 6.4 mm is used for said screening.

17. The process as in claim 16 wherein said diameter is in the range from 0.017 to 0.5 mm.

18. The process as in claim 10 wherein said slurry has a solid p-xylene content in the range below about 55 weight percent.

19. The process as in claim 18 wherein said range is about 1 to 40 weight percent.

20. The process as in claim 10 wherein said filter assembly is substantially of the flat, plate-like configuration.

* * * * *

UNITED STATES PATENT AND TRADEMARK OFFICE
CERTIFICATE OF CORRECTION

PATENT NO. : 4,120,911

DATED : October 17, 1978

INVENTOR(S) : James Melvin Davidson

It is certified that error appears in the above-identified patent and that said Letters Patent are hereby corrected as shown below:

Column 5, line 9, "maintain" should read --maintained--.

Column 6, line 21, "to" first occurrence should read -- up to --

Column 8, line 28, "and" should read --are--.

Column 9, line 61, "had a sensity" should read --has a density--

Signed and Sealed this

Eighth Day of May 1979

[SEAL]

Attest:

RUTH C. MASON
Attesting Officer

DONALD W. BANNER
Commissioner of Patents and Trademarks